US006440082B1

(12) United States Patent
Joo et al.

(10) Patent No.: US 6,440,082 B1
(45) Date of Patent: Aug. 27, 2002

(54) METHOD AND APPARATUS FOR USING HEART SOUNDS TO DETERMINE THE PRESENCE OF A PULSE

(75) Inventors: Tae H. Joo, Redmond; David R. Hampton, Woodinville; James W. Taylor, Redmond; Ronald E. Stickney, Edmonds, all of WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 0 days.

(21) Appl. No.: 09/410,198

(22) Filed: Sep. 30, 1999

(51) Int. Cl.$^7$ ................................................. A61B 5/02
(52) U.S. Cl. ....................... 600/528; 600/483; 600/509; 607/6
(58) Field of Search ............................. 600/483, 493, 600/508, 509, 513, 514, 516, 517, 528, 586; 607/3, 5, 6, 7, 25, 26, 33

(56) References Cited

U.S. PATENT DOCUMENTS

| 4,446,873 | A |   | 5/1984  | Groch et al. |
|-----------|---|---|---------|--------------|
| 4,548,204 | A |   | 10/1985 | Groch et al. |
| 4,559,946 | A |   | 12/1985 | Mower |
| 4,792,145 | A |   | 12/1988 | Eisenberg et al. |
| 4,896,675 | A |   | 1/1990  | Ohsuga et al. |
| 4,967,760 | A | * | 11/1990 | Bennett, Jr. et al. ........ 128/715 |
| 5,077,667 | A |   | 12/1991 | Brown et al. |
| 5,318,592 | A |   | 6/1994  | Schaldach |
| 5,337,752 | A | * | 8/1994  | Reeves ........................ 128/700 |

(List continued on next page.)

FOREIGN PATENT DOCUMENTS

| EP | 0 339 471 A2 | * | 4/1989 | ............ A61N/1/39 |
| EP | 0 339 471 |   | 11/1989 | |
| GB | 2 150 332 |   | 6/1985 | |
| WO | WO 84/01705 |   | 5/1984 | |
| WO | WO 93/22970 |   | 11/1993 | |
| WO | WO 97/05821 |   | 2/1997 | |

OTHER PUBLICATIONS

Bahr et al., "Skills of lay people in checking the carotid pulse," *Resuscitation* 35 (1997) pp. 23–26.

(List continued on next page.)

*Primary Examiner*—Jeffrey R. Jastrzab
*Assistant Examiner*—Frances P. Oropeza
(74) *Attorney, Agent, or Firm*—Christensen O'Connor Johnson Kindness PLLC

(57) ABSTRACT

A method and apparatus determines the presence of a cardiac pulse in a patient by evaluating a physiological signal in the patient, preferably for the presence of characteristic heart sounds. The presence of a heart sound in a patient is determined by analyzing phonocardiogram (PCG) data obtained from the patient. Analyzing the PCG data may include evaluating temporal energy in the PCG data or evaluating spectral energy in the PCG data. Evaluating temporal energy in the PCG data may include estimating a first and second energy in the PCG data and comparing the first and second energy to determine a relative change in energy between them. Evaluating spectral energy in the PCG data may include calculating an energy spectrum of the PCG data and evaluating either the energy value or the frequency of a peak energy in the energy spectrum. The presence of a heart sound may also be determined by combining an evaluation of temporal energy with an evaluation of spectral energy in the PCG data. Electrocardiogram data obtained from the patient may further be used in connection with the PCG data to determine the presence of a cardiac pulse in the patient. An automated external defibrillator processing the physiological signal sensed in the patient automatically reports to an operator of the defibrillator whether a cardiac pulse is determined to be present.

62 Claims, 13 Drawing Sheets

U.S. PATENT DOCUMENTS

| | | | |
|---|---|---|---|
| 5,366,486 A | | 11/1994 | Zipes et al. |
| 5,392,780 A | * | 2/1995 | Ogino et al. ............... 128/670 |
| 5,405,362 A | * | 4/1995 | Kramer et al. ................ 607/5 |
| 5,458,621 A | | 10/1995 | White et al. |
| 5,497,779 A | | 3/1996 | Takaya et al. |
| 5,617,868 A | | 4/1997 | Harada et al. |
| 5,683,424 A | | 11/1997 | Brown et al. |
| 5,685,317 A | * | 11/1997 | Sjostrom ................... 128/715 |
| 5,687,738 A | | 11/1997 | Shapiro et al. |
| 5,700,283 A | * | 12/1997 | Salo ........................... 607/17 |
| 5,704,363 A | | 1/1998 | Amano |
| 5,795,300 A | | 8/1998 | Bryars |
| 5,807,268 A | | 9/1998 | Reeves et al. |
| 5,825,895 A | | 10/1998 | Grasfield et al. |
| 6,125,298 A | * | 9/2000 | Olson et al. ................... 607/5 |
| 6,141,584 A | * | 10/2000 | Rockwell et al. .............. 607/5 |

OTHER PUBLICATIONS

Eberle et al., "Checking the carotid pulse check: diagnostic accuracy of first responders in patients with and without a pulse," *Resuscitation* 33 (1996) pp. 107–116.

Gulcur et al., "Estimation of Systolic Blood Pressure from the Second Heart Sounds," *2$^{nd}$ International Biomedical Engineering Days* (1998) pp. 39–40.

Ochoa et al., "Competence of health professionals to check the carotid pulse," *Resuscitation* 37 (1998) pp. 173–175.

Iwata Akira; Suzumura Nobuo; Ikegaya Kazuo, "Pattern classification of the phonocardiogram using linear prediction analysis," *Medical & Biological Engineering & Computing*, vol. 15, No. 4, pp. 407–412 (Jul. 1977).

Lehner, R.J.; Rangayyan, R.M., "Microcomputer system for quantification of the phonocardiogram," *Proceedings of the Seventh Annual Conference of the IEEE/Engineering in Medicine and Biology Society*, vol. 2, No. 2, pp. 849–854, (1986).

Stodieck, L.S., and M.W. Luttges, "Relationships Between the Electrocardiogram and Phonocardiogram: Potential for Improved Hear Monitoring," *ISA Transactions*, vol. 23, No. 4, pp. 59–65 (Apr. 1984).

Hasegawa, M.D., and S. Rodbard, M.D., Ph.D., "Delayed timing of heart and arterial sounds in patients with implanted pacemakers," *The Journal of Thoracic and Cardiovascular Surgery*, vol. 72, No. 1, pp. 62–66 (Jul. 1976).

Luisada, A.A., M.D., "The First Heart Sound in Normal and Pathological Conditions," *Japanese Heart Journal.*, vol. 28, No. 2, pp. 143–156 (Mar. 1987).

Bulgrin, J.R., B.J. Rubal, C.R. Thompson, and J.M. Moody, "Comparison of short–time Fourier, wavelet and time–domain analyses of intracardiac sounds." *Biomedical Sciences Instrumentation*, vol. 29, pp. 465–472 (1993), ISA Paper #93–059.

\* cited by examiner

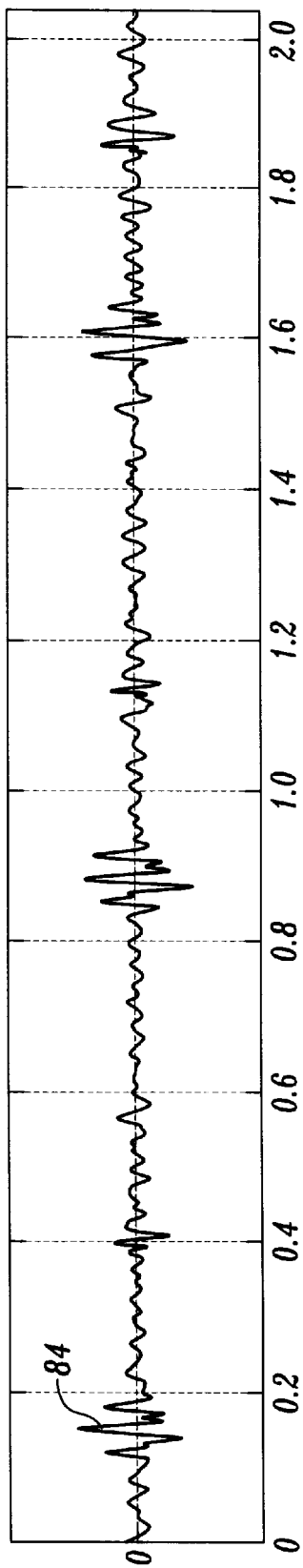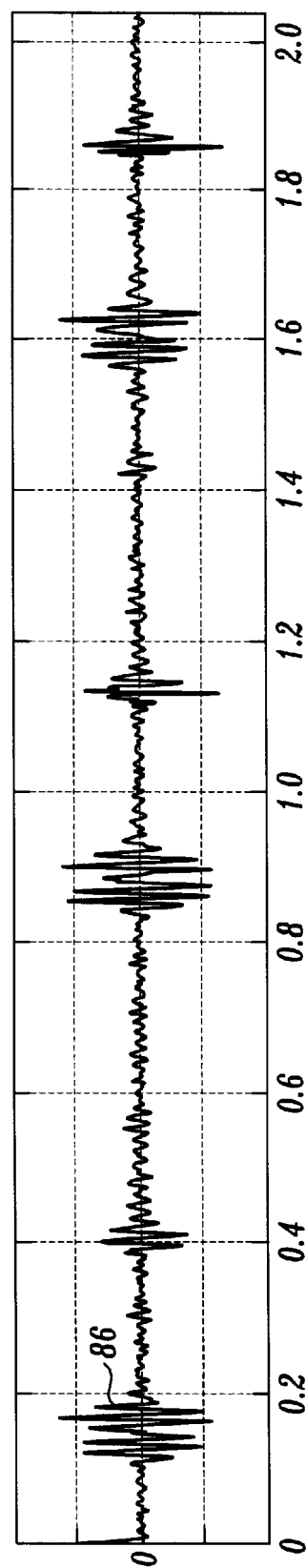

METHOD AND APPARATUS FOR USING HEART SOUNDS TO DETERMINE THE PRESENCE OF A PULSE

FIELD OF THE INVENTION

The invention relates generally to the detection of cardiac activity in a patient, and more specifically, to the detection of a cardiac pulse.

BACKGROUND OF THE INVENTION

The presence of cardiac pulse, or heartbeat, in a patient is often detected by palpating the patient's neck and sensing changes in the volume of the patient's carotid artery due to blood pumped from the patient's heart. A graph representative of the physical expansion and contraction of a patient's carotid artery during two consecutive heartbeats is shown at the top of FIG. 1. When the heart's ventricles contract during a heartbeat, a low-frequency pressure wave is sent throughout the patient's peripheral circulation system. The carotid pulse shown in FIG. 1 rises with the ventricular ejection of blood at systole and peaks when the ejection rate is at its maximum. The carotid pulse falls off again as the pressure subsides toward the end of each pulse.

The opening and closing of the patient's heart valves during a heartbeat causes high-frequency vibrations in the adjacent heart wall and blood vessels. These vibrations can be heard in the patient's body as heart sounds. A conventional phonocardiogram (PCG) transducer placed on a patient converts the acoustical energy of the heart sounds to electrical energy, resulting in a PCG waveform that may be recorded and displayed, as shown by the middle graph in FIG. 1. Conventional methods for detecting and displaying a PCG waveform are well-known in the art. See, e.g., U.S. Pat. Nos. 5,687,738 and 4,548,204.

As indicated by the PCG waveform shown in FIG. 1, a typical heartbeat produces two main heart sounds. The first heart sound, denoted S1, is generated by vibration generally associated with the closure of the tricuspid and mitral valves at the beginning of systole. Typically, the heart sound S1 is about 14 milliseconds long and contains frequencies up to approximately 500 Hz. The second heart sound, denoted S2, is generally associated with vibrations resulting from the closure of the aortic and pulmonary valves at the end of systole. While the duration of the second heart sound S2 is typically shorter than the first heart sound S1, the spectral bandwidth of the heart sound S2 is typically larger than that of S1.

An electrocardiogram (ECG) waveform of a patient is different than a PCG waveform. An ECG waveform describes the electrical activity, rather than the acoustical activity, of a patient's heart. The bottom graph of FIG. 1 illustrates an example of an ECG waveform corresponding in time with the carotid pulse and the PCG waveform.

The lack of a detectable cardiac pulse in a patient can be a strong indicator of cardiac arrest. Cardiac arrest is a life-threatening medical condition in which the electrical activity of a patient's heart becomes unsynchronized, resulting in a loss of the heart's ability to contract and pump blood into the circulation system. A caregiver may apply a defibrillation shock to a patient in cardiac arrest to stop the unsynchronized electrical activity and reinitiate a synchronized perfusing rhythm. External defibrillation, in particular, is provided by applying a strong electric pulse to the patient's heart through electrodes placed on the surface of the patient's body.

Before providing defibrillation therapy to a patient, a caregiver must first confirm that the patient is in cardiac arrest. A defibrillation shock provided to a patient not in cardiac arrest may itself induce lethal cardiac arrhythmias in the patient. In general, external defibrillation is suitable only for patients that are unconscious, apneic (i.e., not breathing), and pulseless. Medical guidelines indicate that the absence of a pulse in a patient should be determined within 5–10 seconds.

Unfortunately, under the pressures of an emergency situation, it can be extremely difficult for first-responding caregivers with little or no medical training to consistently and accurately detect a cardiac pulse in a patient (e.g., by palpating the carotid arteries) in a short amount of time such as 5–10 seconds. Nevertheless, because time is of the essence in treating cardiac arrest, a caregiver may rush the preliminary evaluation, incorrectly conclude that the patient has no pulse, and proceed to provide defibrillation therapy when in fact the patient has a pulse. Alternatively, a caregiver may incorrectly conclude that the patient has a pulse and erroneously withhold defibrillation therapy. A need therefore exists for a method and apparatus that quickly, accurately, and automatically determines the presence of a pulse in a patient, particularly to assist a caregiver in determining whether defibrillation therapy is appropriate in an emergency situation.

SUMMARY OF THE INVENTION

The present invention provides a method and apparatus that determines the presence of a cardiac pulse in a patient by evaluating the patient for the presence of characteristic heart sounds. By physiologically associating the presence of a heart sound with the presence of a cardiac pulse, the presence of a cardiac pulse in the patient is determined.

In accordance with one aspect of the present invention, the presence of a cardiac pulse in a patient is determined by analyzing PCG data obtained from the patient for a feature indicative of the presence of a heart sound and determining from the feature whether a heart sound is present in the patient. Analyzing the PCG data includes evaluating the temporal energy in the PCG data or evaluating the spectral energy in the PCG data. Evaluating the temporal energy in the PCG data may include estimating an instantaneous energy in the PCG data, estimating a background energy in the PCG data, and comparing the estimated instantaneous energy with the estimated background energy. Evaluating the spectral energy in the PCG data may include calculating an energy spectrum of the PCG data, evaluating the energy spectrum to locate a peak energy value, and comparing the peak energy value with a threshold energy value. The frequency at which a peak energy value occurs may also be compared with a threshold frequency. The peak energy value used in this aspect of the invention is preferably the second peak energy value occurring in the energy spectrum measured from DC.

In accordance with another aspect of the present invention, the presence of a cardiac pulse in a patient may be determined by combining an evaluation of the temporal energy in the PCG data with an evaluation of the spectral energy in the PCG data. Electrocardiogram (ECG) data obtained from the patient may also be used in connection with the PCG data to determine the presence of a pulse in the patient. In one approach, if the PCG data appears to indicate the presence of a heart sound, the ECG data is evaluated for the presence of a QRS complex. If the time at which the QRS complex occurs is within an expected time of when the heart sound appeared to occur, a cardiac pulse is determined to be present in the patient. In another approach, the ECG data is evaluated for the presence of a QRS complex to gate the heart sound detection process. If an R-wave occurs in the ECG data, the PCG data should indicate the presence of a heart sound following the R-wave if a cardiac pulse is present. If a heart sound is not detected following an R-wave, the patient may be in a state of pulseless electrical activity (PEA).

In yet another aspect, the present invention provides a medical device with at least one electrode adapted to sense PCG signals in a patient, a conversion circuit for converting the PCG signals into digital PCG data, and a processing unit for processing the PCG data to determine a feature indicative of the presence of a heart sound in the patient. The processing unit determines the presence of a heart sound in the patient based on the determined feature. The medical device may further include a defibrillation pulse generator for providing a defibrillation pulse to the patient, and an input device that allows the operator of the device to initiate delivery of the defibrillation pulse, if defibrillation therapy is appropriate.

The medical device may determine the presence of a heart sound in the patient by evaluating the temporal energy in the PCG data or the spectral energy in the PCG data, or both. The medical device may also be provided with ECG electrodes adapted to sense ECG signals in the patient. The processing unit evaluates ECG data in combination with the PCG data to determine whether a cardiac pulse is present in the patient. A display is included for prompting messages to the operator of the device. When implemented in an automated external defibrillator, physiological data, such as PCG data, obtained from the patient is automatically evaluated for the presence of a cardiac pulse to assist in determining whether a defibrillation pulse should be applied to the patient.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 5A is a graph illustrating a PCG waveform of raw PCG data collected from a patient;

FIG. 5B is a graph illustrating a filtered version of the PCG waveform shown in FIG. 5A;

DETAILED DESCRIPTION OF THE PREFERRED EMBODIMENT

Figure 1:
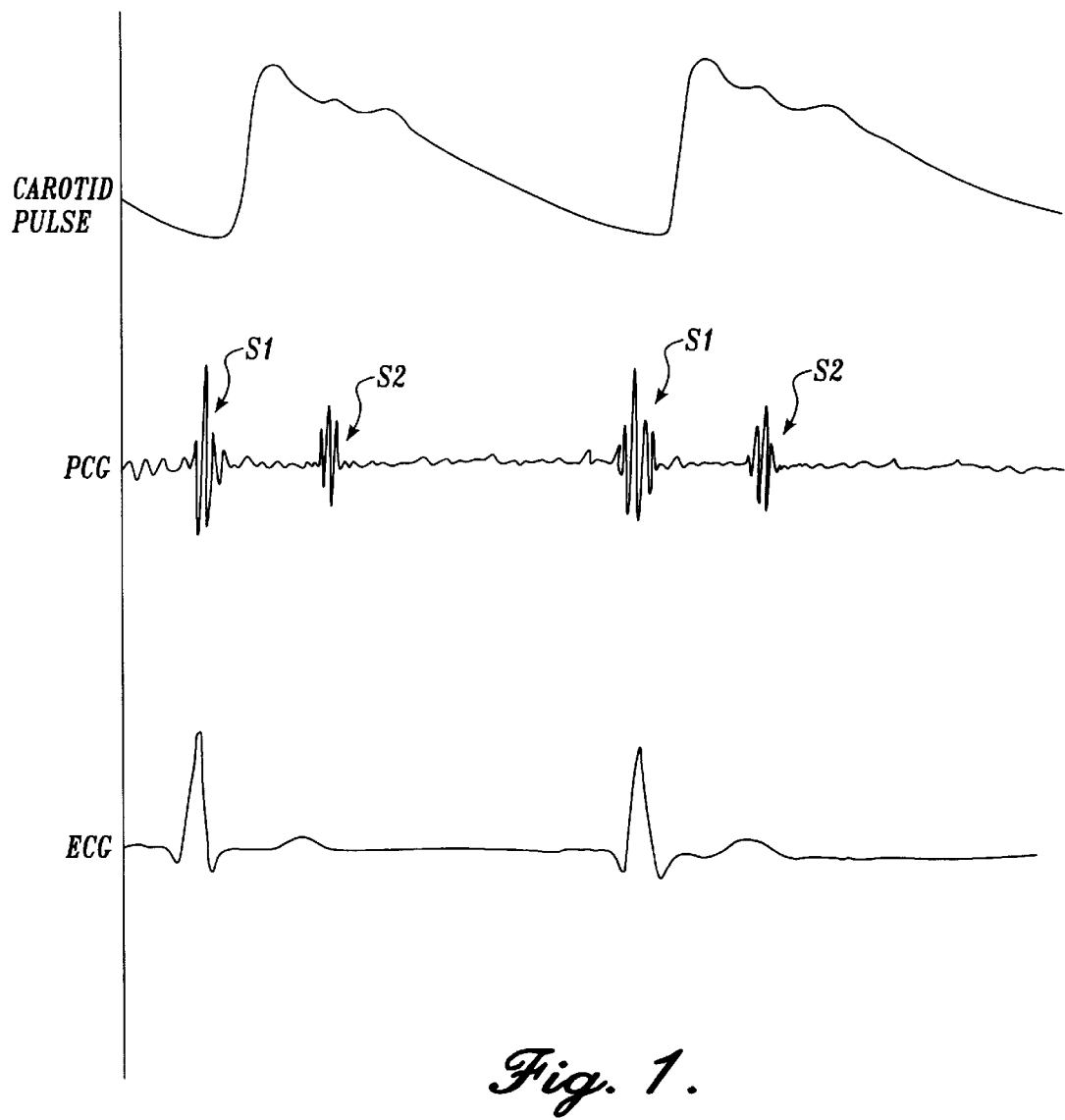
FIG. 1 is a pictorial diagram of a carotid pulse waveform, a phonocardiogram (PCG) waveform, and an electrocardiogram (ECG) waveform for two consecutive heartbeats.
Figure 2:
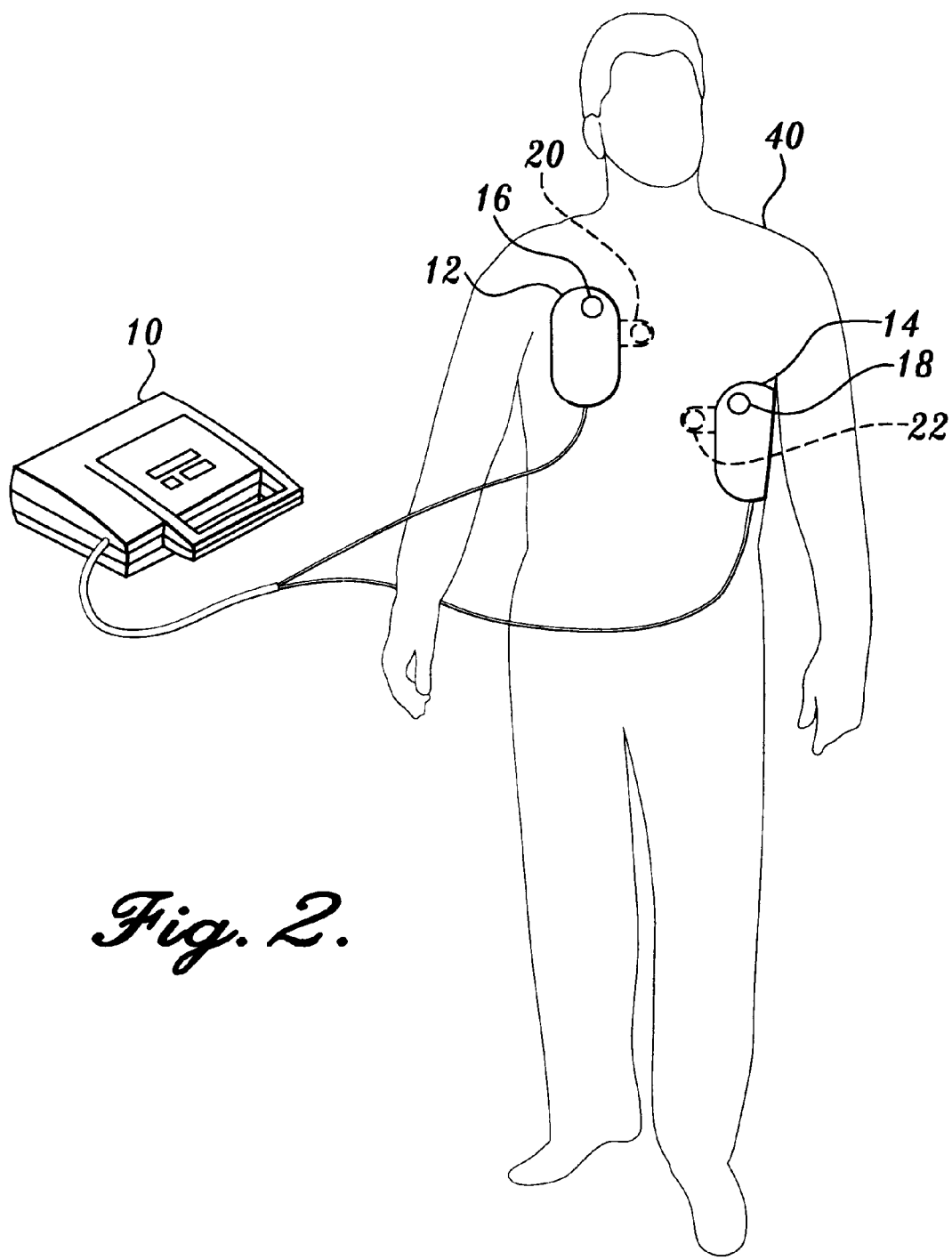
FIG. 2 is a pictorial diagram of a defibrillator and electrodes constructed in accordance with the present invention and attached to a patient.

Although the present invention may be implemented in a variety of applications, the present invention is particularly suited for use in a defibrillator, such as the defibrillator 10 shown in FIG. 2. In FIG. 2, the defibrillator 10 is shown connected to a patient 40 via defibrillation electrodes 12 and 14 placed on the skin of the patient 40. The defibrillator 10 uses the defibrillation electrodes 12 and 14 to deliver defibrillation pulses to the patient 40. The defibrillator 10 may also use the electrodes 12 and 14 to obtain ECG signals from the patient 40.

FIG. 2 also illustrates sensing devices 16 and 18 placed on the patient 40. The sensing devices 16 and 18 are configured to detect a physiological signal in the patient, preferably acoustical energy from heart sounds produced in the patient 40. The acoustical energy is converted by the defibrillator 10 into digital phonocardiogram (PCG) data. The sensing devices 16 and 18 may be integrated into or attached to the back of the electrodes 12 and 14. Alternatively, the sensing devices 16 and 18 may be embodied in flaps 20 and 22 that are connected to the electrodes 12 and 14. As another alternative, the sensing devices 16 and 18 may be attached to the patient 40 by separate wires (not shown).

In one embodiment of the invention, the sensing devices 16 and 18 are comprised of piezoelectric transducers. The sensing devices 16 and 18 may alternatively be comprised of other acoustic sensors known in the art, such as electronic microphones used in stethoscopes. Transducers and microphones suitable for use in the present invention for detecting heart sounds are described, for example, in U.S. Pat. Nos. 4,446,873 and 5,825,895.

While the embodiment of the invention specifically described herein is implemented in a defibrillator 10, the present invention is not limited to such specific application. It will be recognized that the advantages of the invention may be achieved by implementing the present invention in cardiac monitors and other medical equipment that do not necessarily provide defibrillation therapy.

Figure 3:
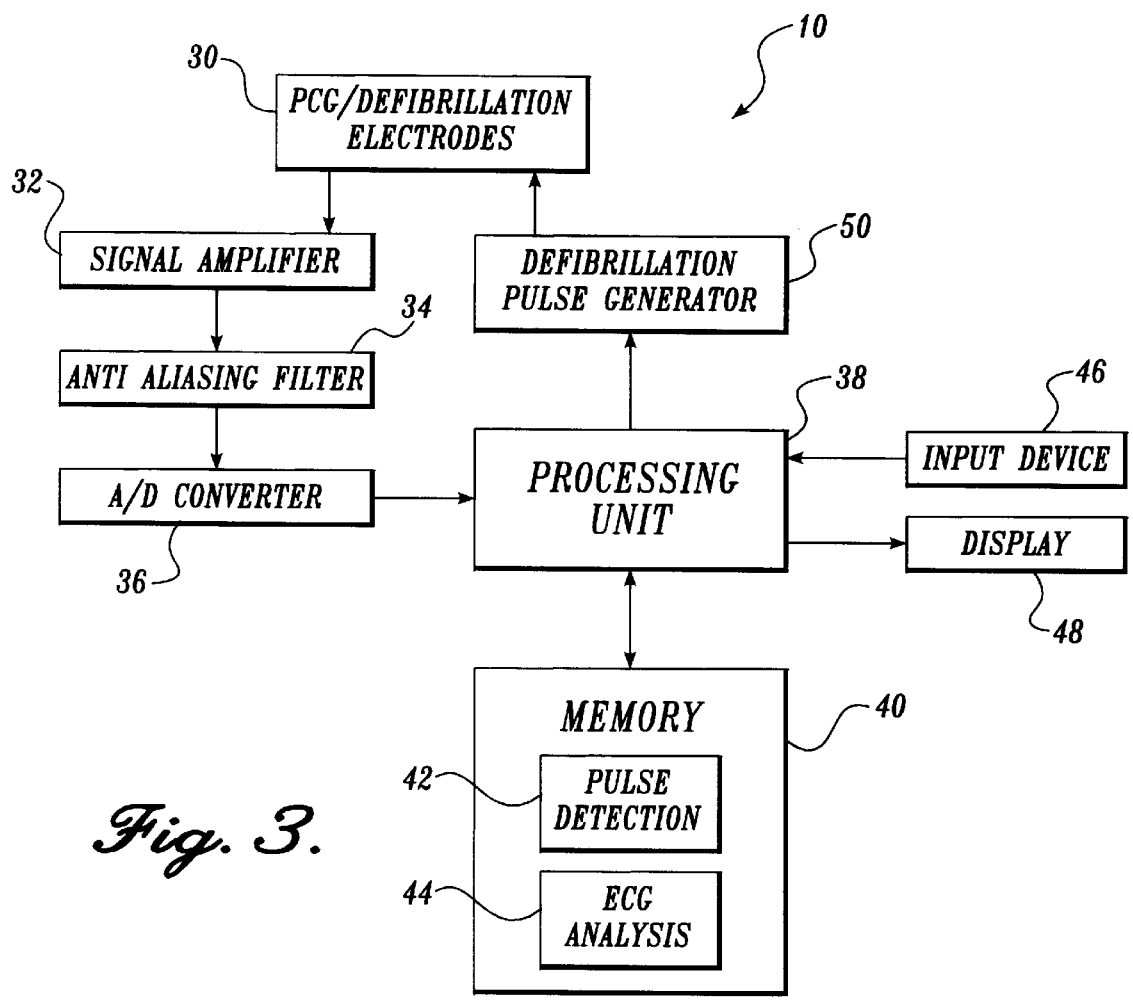
FIG. 3 is a block diagram of the major components of the defibrillator shown in FIG. 2.

FIG. 3 illustrates in more detail the major components of the defibrillator 10 shown in FIG. 2. In FIG. 3, a patient's heart sounds are sensed by PCG/defibrillation electrodes 30 (e.g., a combination of electrodes 12 and 14 with sensing devices 16 and 18, as described above in reference to FIG. 2) and converted to PCG signals in a conventional manner. The PCG/defibrillation electrodes 30 provide the PCG signals to a signal amplifier 32 that amplifies the PCG signals to a level sufficient for the defibrillator 10 to further analyze the PCG signals. Alternative embodiments of the defibrillator 10 may include additional signal amplification or signal filtering to adapt the defibrillator 10 for use in particular environments.

The signal amplifier 32 provides the amplified PCG signals to an anti-aliasing filter 34. The anti-aliasing filter 34 is designed to reduce aliasing introduced in the PCG signals by the analog-to-digital (A/D) converter 36. The bandwidth of the anti-aliasing filter 34 depends, in part, on the sampling rate of the A/D converter 36. Anti-aliasing filters and A/D converters are well-known in the art and are readily available in off-the-shelf devices. The A/D converter 36 converts the PCG signals into digitized PCG data and provides the PCG data to a processing unit 38 for evaluation.

The processing unit 38 evaluates the PCG data using a pulse detection process described below in more detail. The processing unit 38 is preferably comprised of a computer processor that operates in accordance with programmed instructions 42 stored in a memory 40 that implement the pulse detection process. Preferably, the processing unit 38 also stores the PCG data in the memory 40. The memory 40 may be comprised of any type of storage medium including, for example, a volatile memory such as a random access memory (RAM), a non-volatile static memory, or a magnetic or optical storage medium (e.g., tape or hard drive).

The processing unit 38 may report the results of the pulse detection process to the operator of the defibrillator 10 via a display 48. The display 48 may include, for example, lights, audible signals, a printer, or a display screen (e.g., LCD or AMLCD). The processing unit 38 may also receive input from the operator of the defibrillator 10 via an input device 46. The input device 46 may include one or more keys, switches, buttons, or other types of user input devices.

The defibrillator 10 may also use the PCG/defibrillation electrodes 30 to sense the patient's electrocardiogram (ECG) signals. The signals obtained from the patient are amplified and filtered by the signal amplifier 32 and further filtered by the anti-aliasing filter 34 in a conventional manner. The A/D converter 36 converts the ECG signals into digitized ECG data and provides the ECG data to the processing unit 38 for evaluation.

Preferably, the processing unit 38 evaluates the ECG signals in accordance with programmed instructions 44 stored in the memory 40 that carry out an ECG evaluation process to determine whether a defibrillation shock should be provided. A suitable method for determining whether to apply a defibrillation shock is described in U.S. Pat. No. 4,610,254, which is assigned to the assignee of the present invention and incorporated by reference herein. If the processing unit 38 determines that delivery of a defibrillation pulse is appropriate, the processing unit 38 instructs a defibrillation pulse generator 50 to prepare to deliver a defibrillation pulse to the patient. In that regard, the defibrillation pulse generator 50 charges one or more defibrillation capacitors in the defibrillator 10.

When the defibrillation charge is ready for delivery, the processing unit 38 advises the operator (e.g., via the display 48) that the defibrillator 10 is ready to deliver the defibrillation pulse. Preferably, the processing unit 38 asks the operator to initiate the delivery of the defibrillation pulse. When the operator initiates delivery of the defibrillation pulse (e.g., by initiating the input device 46), the processing unit 38 instructs the defibrillation pulse generator 50 to discharge through the patient the energy stored in the defibrillation capacitors (via the PCG/defibrillation electrodes 30). Alternatively, the processing unit 38 may cause the defibrillation pulse generator 50 to automatically deliver the defibrillation pulse when specified conditions (e.g., expiration of a predetermined period of time, acceptable measured patient impedance, etc.) are met.

While FIG. 3 illustrates the major components of the defibrillator 10, those having ordinary skill in the art will appreciate that the defibrillator 10 may contain more components than those shown in FIG. 3. However, the disclosure of a preferred embodiment of the defibrillator 10 does not require that all of these general conventional components be shown. It will further be appreciated that the invention may be implemented in a cardiac monitor having essentially the same components as the defibrillator 10 shown in FIG. 3, except that the cardiac monitor does not have the components necessary for delivering a defibrillation pulse. Moreover, the programmed instructions 42 may be encoded in hardware as an alternative to software instructions stored in the memory 40.

The pulse detection process conducted by the processing unit 38 (using programmed instructions 42) analyzes the patient's PCG data to determine whether heart sounds S1 and/or S2 are present. In accordance with the present invention, the presence of heart sounds S1 and/or S2 are used as a surrogate to indicate the presence of a cardiac pulse in the patient. Hence, if the pulse detection process detects heart sounds in the patient's PCG, the pulse detection process determines that a pulse is present in the patient.

Figure 4:
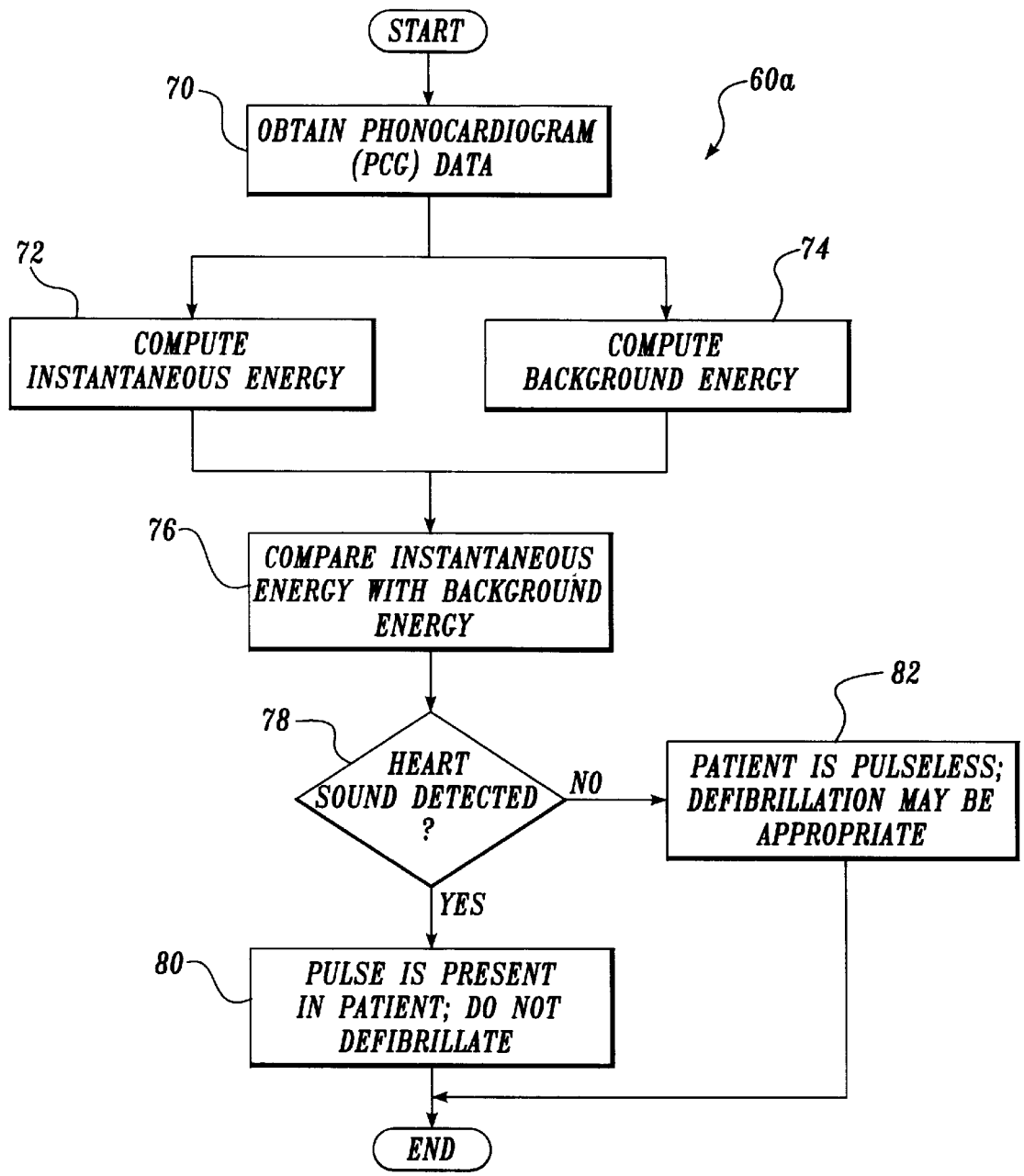
FIG. 4 is a flow diagram of a pulse detection process performed by a defibrillator as shown in FIG. 2, wherein a temporal energy analysis of PCG data is performed.

FIG. 4 illustrates one version of the pulse detection process 60a using a temporal energy analysis conducted in accordance with the present invention. In FIG. 4, the pulse detection process 60a begins in a block 70 by obtaining PCG data from a patient. As noted earlier, PCG signals obtained by PCG sensing devices (e.g., sensing devices 16 and 18 in FIG. 2) placed on the patient are converted into digital PCG data.

The pulse detection process 60a evaluates the PCG data for at least one feature indicative of the presence of a heart sound. In blocks 72 and 74, the pulse detection process 60a preferably calculates estimates of the instantaneous energy and background energy in the PCG data. As shown in FIG. 4, the estimated instantaneous energy may be calculated in block 72 simultaneously with the calculation of estimated background energy in block 74. Alternatively, the calculation of estimated instantaneous energy in block 72 may be performed prior to or after the calculation of estimated background energy in block 74.

The estimated instantaneous energy is calculated in block 72, preferably using a set of PCG data obtained from the patient during a predetermined time window. In one actual embodiment of the invention, the time window is 20 milliseconds in length, though a longer, shorter, or slightly shifted time window may be used for estimating the instantaneous energy. The estimated instantaneous energy is preferably calculated by squaring and summing each of the PCG data values in the predetermined time window.

The estimated background energy is calculated in block 74, preferably using a set of PCG data obtained in an earlier predetermined time window. In one actual embodiment of the invention, the estimated background energy is calculated using PCG data in a 20 millisecond time window commencing 50 milliseconds prior to the current time. The PCG data within the earlier time window are also preferably squared and summed to produce the estimated background energy.

The estimated instantaneous energy and background energy are next compared in a block 76 to determine a relative change in energy in the PCG data. The relative change in energy is used by the pulse detection process 60a as a feature indicative of the presence of a heart sound. If the relative change in energy between the estimated instantaneous energy and the estimated background energy exceeds a predetermined threshold, the pulse detection process 60a determines that a heart sound was detected.

As noted earlier, the present invention uses the detection of a heart sound as an indication of the presence of a cardiac pulse in the patient. In a decision block 78, if a heart sound was detected, the pulse detection process 60a proceeds to a block 80 and reports the presence of a cardiac pulse in the patient (thus indicating that defibrillation therapy for the patient is not advised). Otherwise, if a heart sound is not detected, the pulse detection process 60a determines in a block 82 that the patient is pulseless and that defibrillation therapy may be appropriate. A defibrillator 10 implementing the pulse detection process 60a may then proceed to determine whether defibrillation therapy is appropriate, e.g., by obtaining and processing ECG data from the patient as described in U.S. Pat. No. 4,610,254, referenced earlier.

In a further embodiment of the invention, the pulse detection process 60a may be repeated over a specified interval of time or for a specified number of repetitions to produce a series of determinations of whether a heart sound is present in the patient. The time windows for computing the estimated instantaneous energy and background energy are shifted to correspond with each instance of time in which the pulse detection process 60a is performed. The pulse detection process 60a may require a specified number of heart sound detections before determining that a cardiac pulse is present in the patient.

Figure 5C:
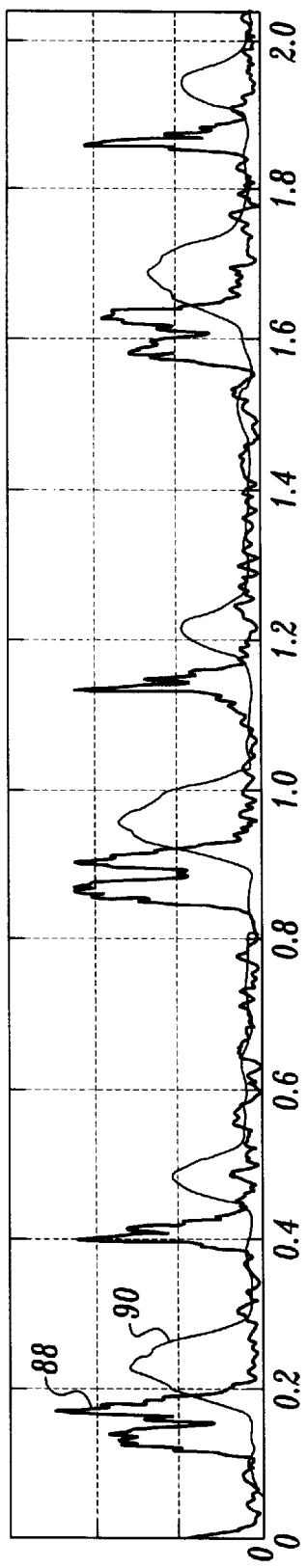
FIG. 5C is a graph illustrating an instantaneous energy waveform and the background energy waveform computed from the data in the PCG waveform shown in FIG. 5B in accordance with the pulse detection process shown in FIG. 4.

FIGS. 5A–5D illustrate a representative example of the processing performed by the pulse detection process 60a. In particular, FIG. 5A is a graph showing a PCG waveform 84 of raw PCG data as collected in block 70 (FIG. 4) from a patient. As noted above, the PCG data may be filtered to reduce noise and other signal contaminants. A filtered version of the PCG waveform 86 is shown in FIG. 5B.

FIG. 5C illustrates a waveform 88 depicting the estimated instantaneous energy in the PCG as calculated in block 72 of the pulse detection process 60a. The waveform 90 depicts the estimated background energy as calculated in block 74 of the pulse detection process 60a. Because the calculation of background energy 90 uses PCG data obtained in an earlier time window than the PCG data used to calculate instantaneous energy 88, the rise and fall of the background energy waveform 90 follows the rise and fall of the instantaneous energy waveform 88.

Figure 5D:
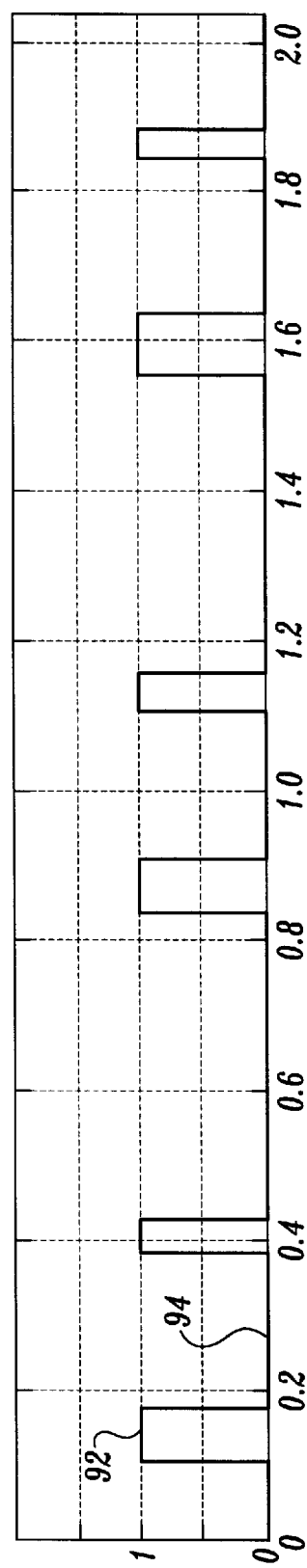
FIG. 5D is a graph illustrating the results of a comparison of the instantaneous energy and the background energy shown in FIG. 5C in accordance with the pulse detection process shown in FIG. 4.

The comparison performed in block 76 of the pulse detection process 60a may produce a result as illustrated in FIG. 5D. During the time in which the instantaneous energy 88 exceeds the background energy 90 by a predetermined threshold, the comparison performed in block 76 returns a "1" (signifying the detection of a heart sound), as noted by reference numeral 92. The predetermined threshold may be adjusted to achieve a desired sensitivity and specificity of detection. When the relative change in energy between the instantaneous energy 88 and the background energy 90 does not exceed the predetermined threshold, the comparison performed in block 76 returns a "0", as noted by reference number 94, signifying that a heart sound was not detected.

Figure 6:
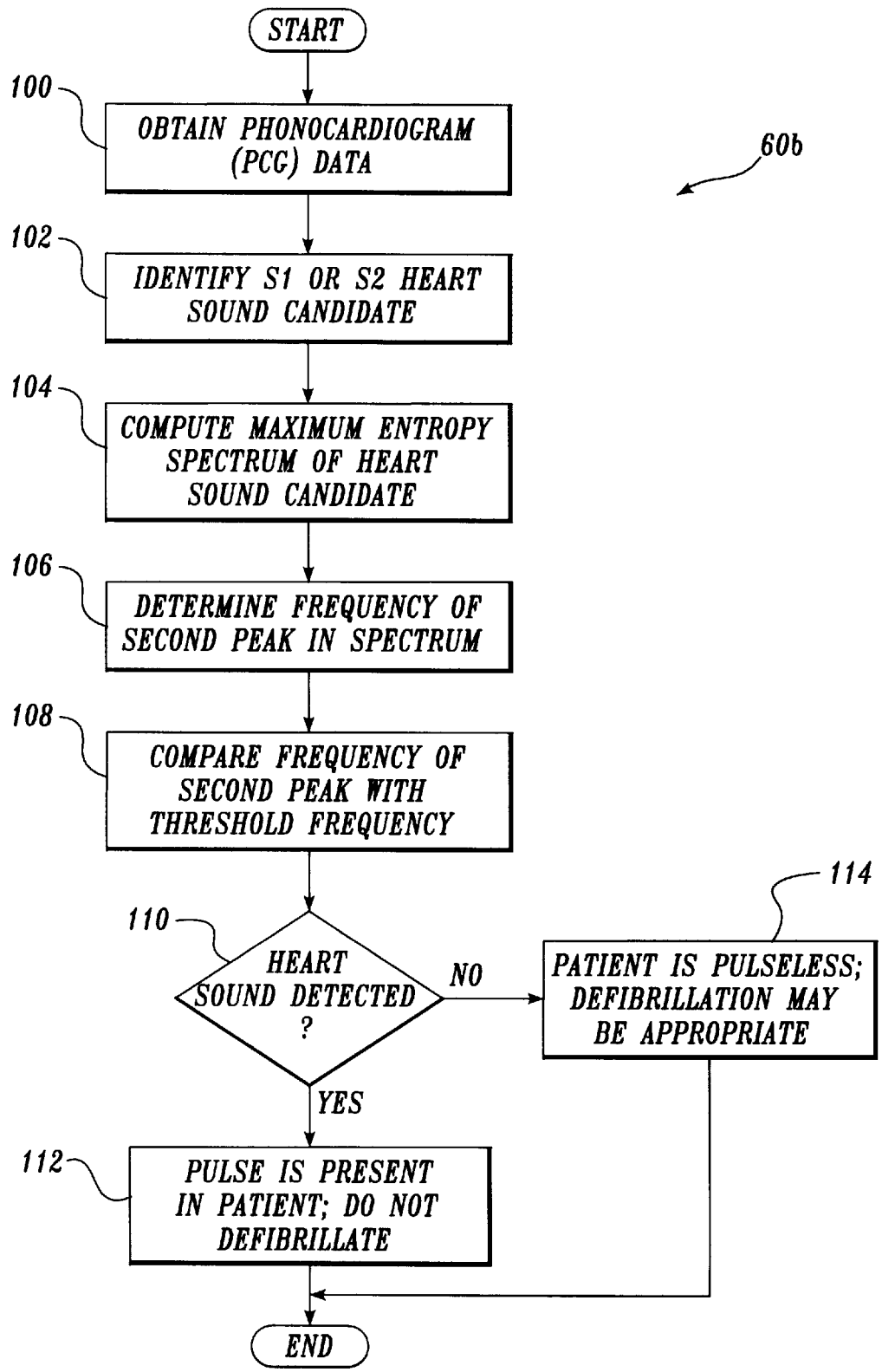
FIG. 6 is a flow diagram of another version of the pulse detection process performed by a defibrillator as shown in FIG. 2, wherein a spectral peak frequency analysis of PCG data is performed.

FIG. 6 illustrates another version of the pulse detection process 60b. As with the version 60a of the pulse detection process, the version 60b analyzes PCG data to detect heart sounds in a patient. If heart sounds are detected, the pulse detection process 60b determines that a pulse is present in the patient. The version 60b of the pulse detection process, however, focuses on a spectral energy analysis of the PCG data (as compared to the temporal energy analysis performed in the version 60a).

The pulse detection process 60b begins in a block 100 by obtaining PCG data from the patient in a manner as discussed above with respect to block 70 (FIG. 4). In a block 102, the PCG data is preferably analyzed to identify a set of PCG data that likely contains an S1 or S2 heart sound. In that regard, an S1 or S2 heart sound candidate may be identified by using the energy comparison discussed in block 76 of the pulse detection process 60a. When the estimated instantaneous energy exceeds the estimated background energy by a predetermined threshold, the energy comparison indicates that a potential S1 or S2 candidate has been detected. Alternatively, a set of PCG data containing a heart sound may be identified by evaluating the patient's ECG data for the occurrence of an R-wave. The timing of an S1 or S2 heart sound in relation to an R-wave is generally known in the art and may be used to predict the timing of a heart sound candidate in the PCG data.

Next, in a block 104, the pulse detection process 60b computes an energy spectrum of the heart sound candidate, preferably using a maximum entropy method. Computing an energy spectrum using a maximum entropy method ("MEM spectrum") is well-known in the art. See, e.g., *Modern Spectral Estimation: Theory and Application*, by Stephen M. Kay, published by Prentice Hall of Englewood Cliffs, N.J., p. 182, incorporated herein by reference. An MEM spectrum typically appears much smoother than an energy spectrum produced by Fourier transform techniques.

Figure 7:
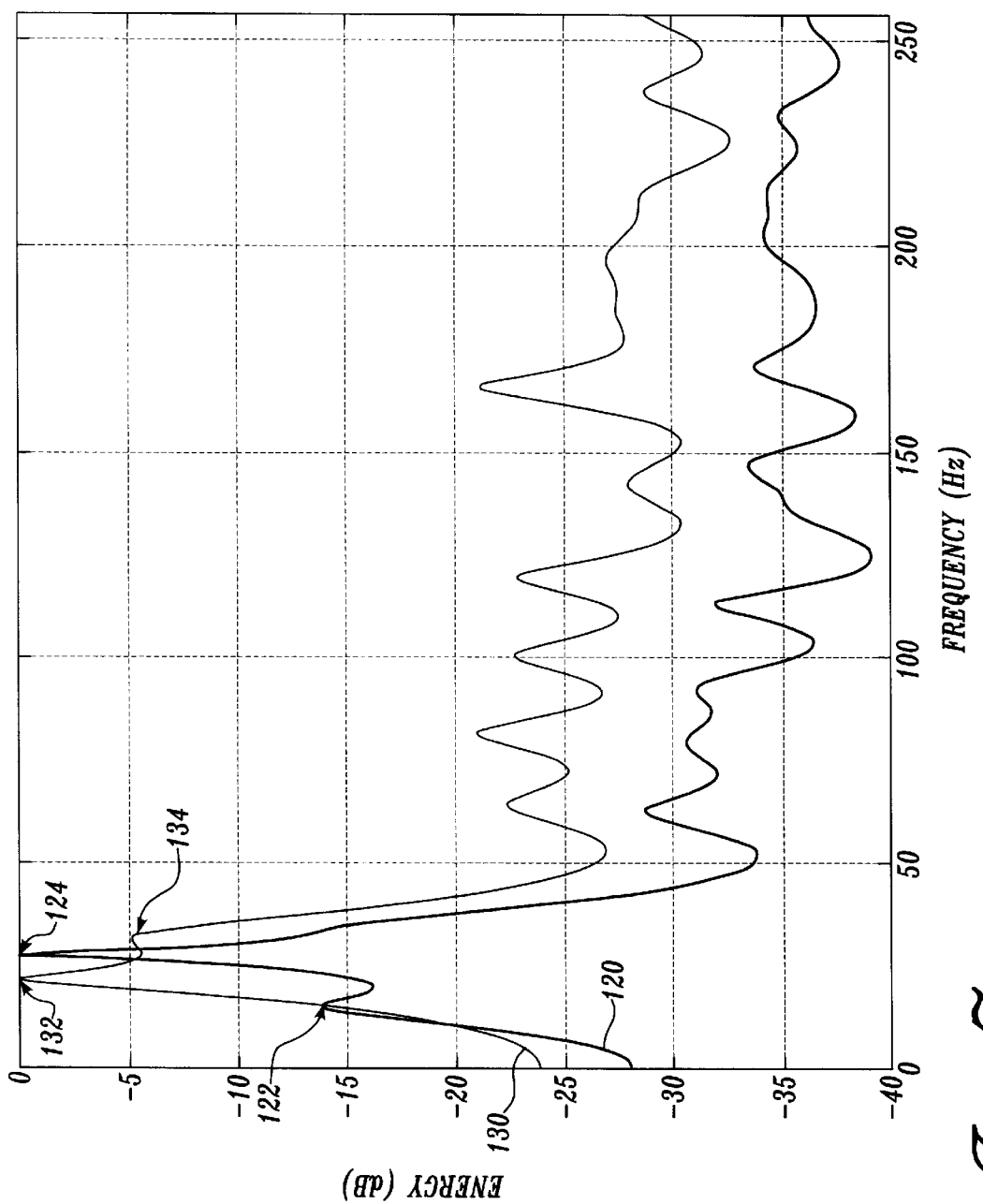
FIG. 7 is a graph illustrating two energy spectra calculated from PCG data using a maximum entropy method ("MEM spectra") in accordance with the pulse detection process shown in FIG. 6.

FIG. 7 illustrates a representative MEM spectrum 120 for an interval of PCG data containing an S1 heart sound. FIG. 7 also illustrates a representative MEM spectrum 130 for a set of PCG data containing an S2 heart sound. The MEM spectrum 120 includes a number of peak energy values, including the first two peak values 122 and 124. Likewise, the MEM spectrum 130 includes a number of peak energy values, including the first two peak values 132 and 134. The MEM spectrum 120 or 130, whichever is used, may be normalized by removing the baseline (DC) energy value across the MEM spectrum.

As will be discussed in more detail below, the frequency of a peak energy value in the energy spectrum is used as a feature indicative of the presence of a heart sound, and is evaluated against a predetermined threshold frequency value to decide whether a heart sound is detected. Preferably, the pulse detection process 60b in FIG. 6 evaluates the second peak energy value occurring in the energy spectrum measured from DC, e.g., the second peak value 124 in the MEM spectrum 120, or the second peak value 134 in the MEM spectrum 130.

In a block 106, the pulse detection process 60b evaluates the energy values in the MEM spectrum to determine the frequency of the second peak in the MEM spectrum. For example, if the pulse detection process 60b evaluates MEM spectrum 120, the frequency of the second peak 124 is determined. A similar analysis applied to the MEM spectrum 130 determines the frequency of the second peak 134.

In a block 108, the frequency of the second peak 124 or 134 is compared with a predetermined threshold frequency to decide whether a heart sound is detected. For example, if the frequency of the second peak 124 or 134 is less than or equal to a threshold frequency, e.g., 100 Hz, the pulse detection process 60b determines that a heart sound was detected. Alternative embodiments of the invention may use values other than 100 Hz for the predetermined threshold frequency.

If a heart sound was detected, the pulse detection process 60b proceeds from decision block 110 to a block 112 and determines that a pulse is present in the patient, thus advising against application of a defibrillation pulse. If, in decision block 110, a heart sound was not detected, the pulse detection process 60b determines in a block 114 that the patient is pulseless and that defibrillation may be appropriate for the patient. In that case, further signal processing of ECG data obtained from the patient is preferably performed to determine the applicability of defibrillation therapy, e.g., as described in U.S. Pat. No. 4,610,254, referenced earlier.

Figure 8A:
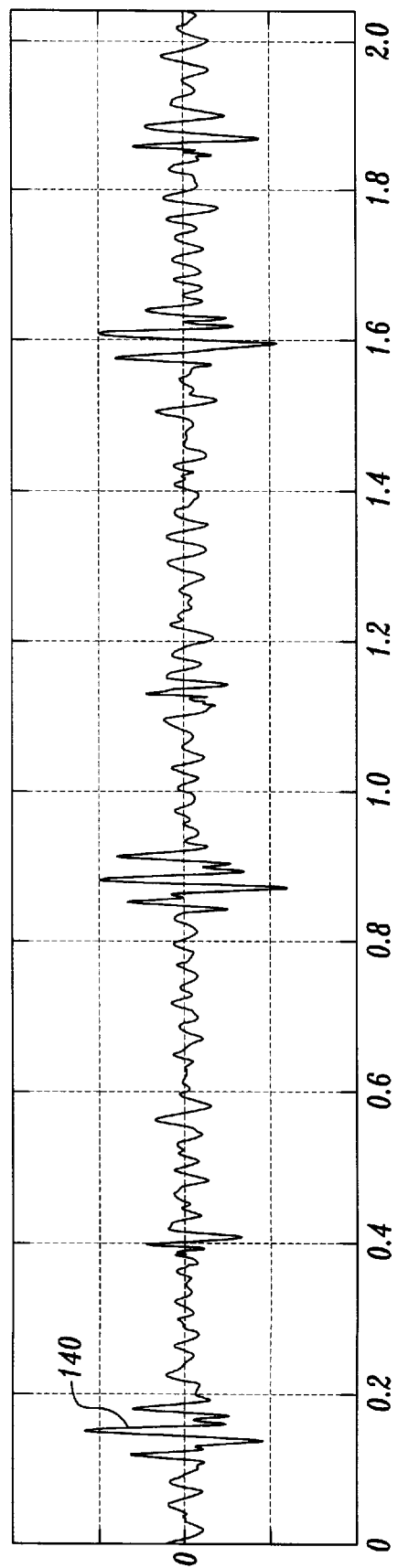
FIG. 8A is a graph illustrating a PCG waveform of raw PCG data collected from a patient.
Figure 8B:
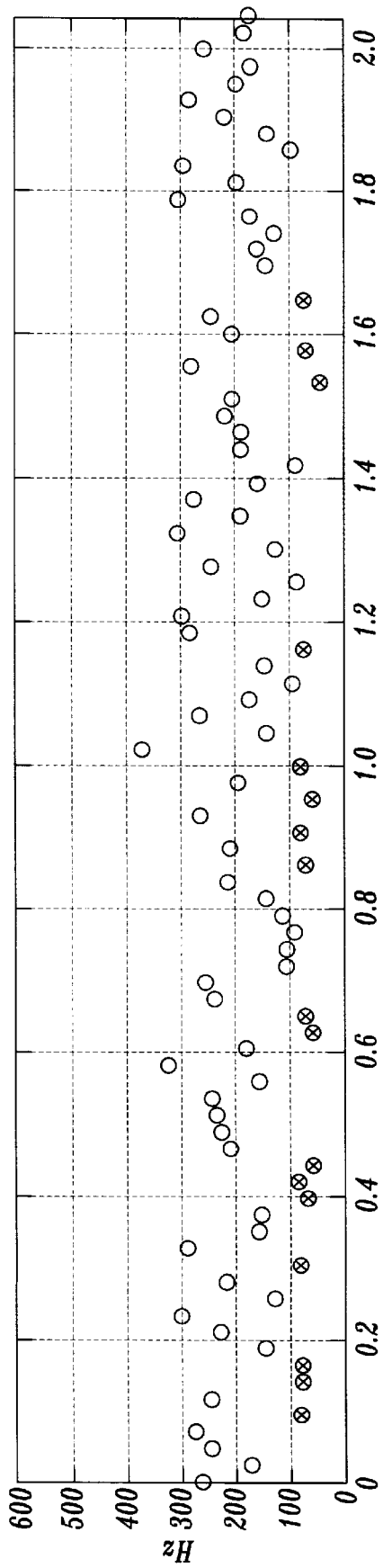
FIG. 8B is a graph illustrating a series of frequencies of second peak energy values located in MEM spectra computed in accordance with the pulse detection process shown in FIG. 6 using the PCG data shown in FIG. 8A, wherein the frequency values at or below a frequency of 100 Hz are marked with an "x"

One example illustrating the processing performed by the pulse detection process 60b is shown in FIGS. 8A and 8B. FIG. 8A is a graph depicting a PCG waveform 140 of raw PCG data obtained from a patient in a manner as discussed above in regard to block 100 (FIG. 6). Although not shown in FIG. 8, the PCG waveform 140 may be filtered to reduce noise and other signal contaminants (e.g., as described earlier in reference to FIG. 5B).

For purposes of demonstrating the invention in FIG. 8B, an MEM spectrum of the data in the PCG waveform 140 is computed for a number of instances in time, and the frequency of the second peak of each MEM spectrum is identified, as shown by the circles in FIG. 8B, without regard to whether the selected instance of time corresponds with a heart sound candidate. Of course, in actual operation where results are needed for immediate and accurate evaluation of a patient rather than hindsight evidence of efficacy, it is preferable in actual operation of the invention that the PCG data first be screened for heart sound candidates.

In FIG. 8B, the circles enclosing an "x" identify the MEM spectra that, for this example, have a second peak located at or below a threshold frequency of 100 Hz. Note that, for the most part, the circles with an "x" in FIG. 8B correspond in time with the heart sounds evident in the PCG waveform 140 shown in FIG. 8A. For each circled "x," the pulse detection process 60b decides that a heart sound, and thus a pulse, is present in the patient.

Figure 9:
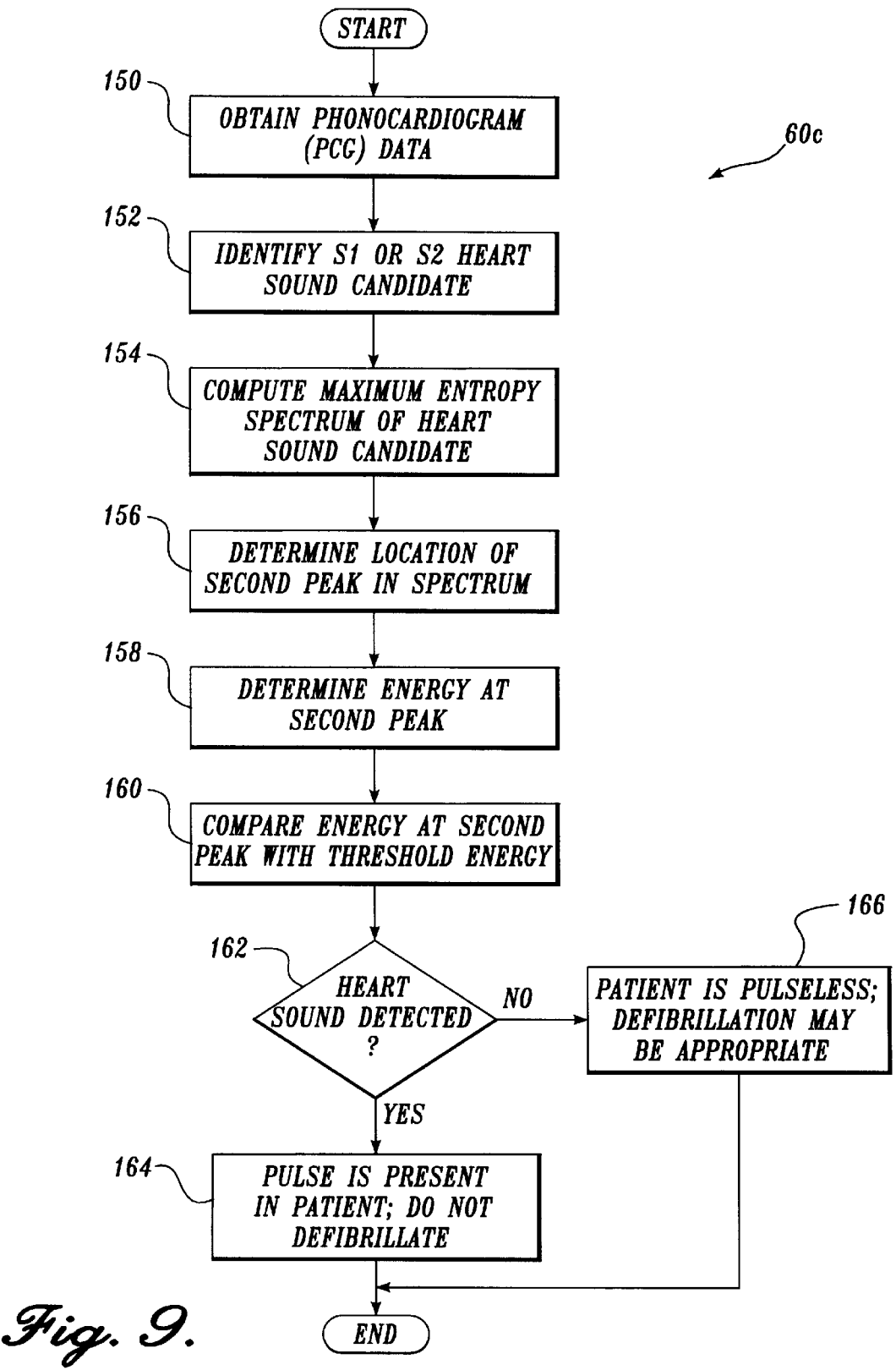
FIG. 9 is a flow diagram illustrating another version of a pulse detection process performed by a defibrillator as shown in FIG. 2, wherein a spectral peak energy analysis is performed.

FIG. 9 illustrates another version 60c of the pulse detection process that also uses an MEM spectrum as calculated in block 104 of the version 60b. Instead of analyzing the frequency location of the second peak in the MEM spectrum, as performed in the version 60b, the version 60c analyzes the energy value of the second peak in the MEM spectrum.

The version 60c of the pulse detection process begins in a block 150 by obtaining PCG data from the patient in a manner as discussed earlier with respect to block 70 (FIG. 4). The PCG data is analyzed in a block 152 to identify PCG data corresponding to the time when a heart sound S1 or S2 likely occurred. The analysis performed in block 152 may include an energy comparison process or ECG analysis as described earlier with respect to block 102 of pulse detection process 60b (FIG. 6). An MEM spectrum of the heart sound candidate is then computed in a block 154 in a manner as discussed earlier with respect to block 104 (FIG. 6).

In a block 156, the pulse detection process 60c evaluates the energy values in the MEM spectrum to locate the second peak value in the spectrum. The energy value of the second peak, determined in a block 158, is used as a feature indicative of the presence of a heart sound, and is compared in a block 160 with a threshold energy to decide whether a heart sound was detected. If the energy value of the second peak exceeds the threshold energy, the pulse detection process 60c determines in a decision block 162 that a heart sound was detected.

If, in decision block 162, a heart sound was detected, the pulse detection process 60c determines in a block 164 that a cardiac pulse is present in the patient and advises against providing defibrillation therapy to the patient. On the other hand, if a heart sound was not detected in decision block 162, the pulse detection process 60c determines in a block 166 that the patient is pulseless and advises that defibrillation therapy may be appropriate for the patient. An analysis of ECG data, as noted earlier, may be used to determine the applicability of defibrillation therapy.

Figure 8C:
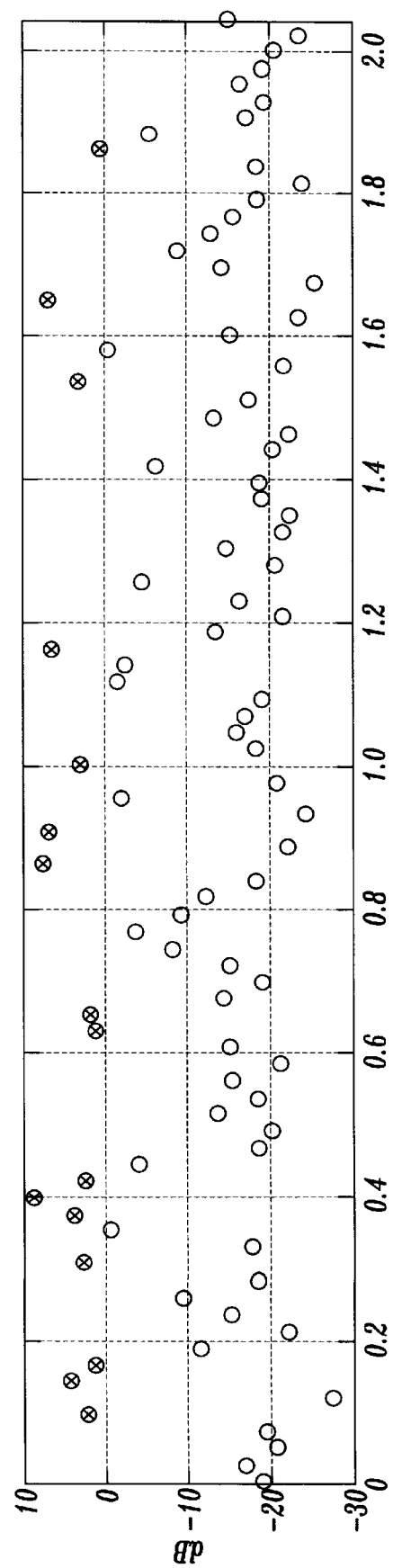
FIG. 8C is a graph illustrating a series of second peak energy values located in MEM spectra computed in accordance with the pulse detection process shown in FIG. 9 using the PCG data shown in FIG. 8A, wherein the second peak energy values exceeding 0 dB are marked with an "x"

FIGS. 8A and 8C illustrate one example of the processing performed by the pulse detection process 60c. As discussed earlier, FIG. 8A illustrates a PCG waveform 140 of raw PCG data obtained from a patient from which an MEM spectrum is computed for a number of instances in time. For each instance in time, the energy value of the second peak in the MEM spectrum is identified, as depicted by the circles in FIG. 8C.

In FIG. 8C, the circles enclosing an "x" are the MEM spectra with a second peak having an energy value above a selected threshold energy, e.g., 0 dB. While a threshold value of 0 dB is used in this specific example, other embodiments of the invention may use different threshold values. The circles with an "x" in FIG. 8C generally correspond in time with the heart sounds evident in the PCG waveform 140 shown in FIG. 8A. Thus, for each circled "x," the pulse detection process 60c decides that a heart sound, and hence a cardiac pulse, is present in the patient.

Figure 10:
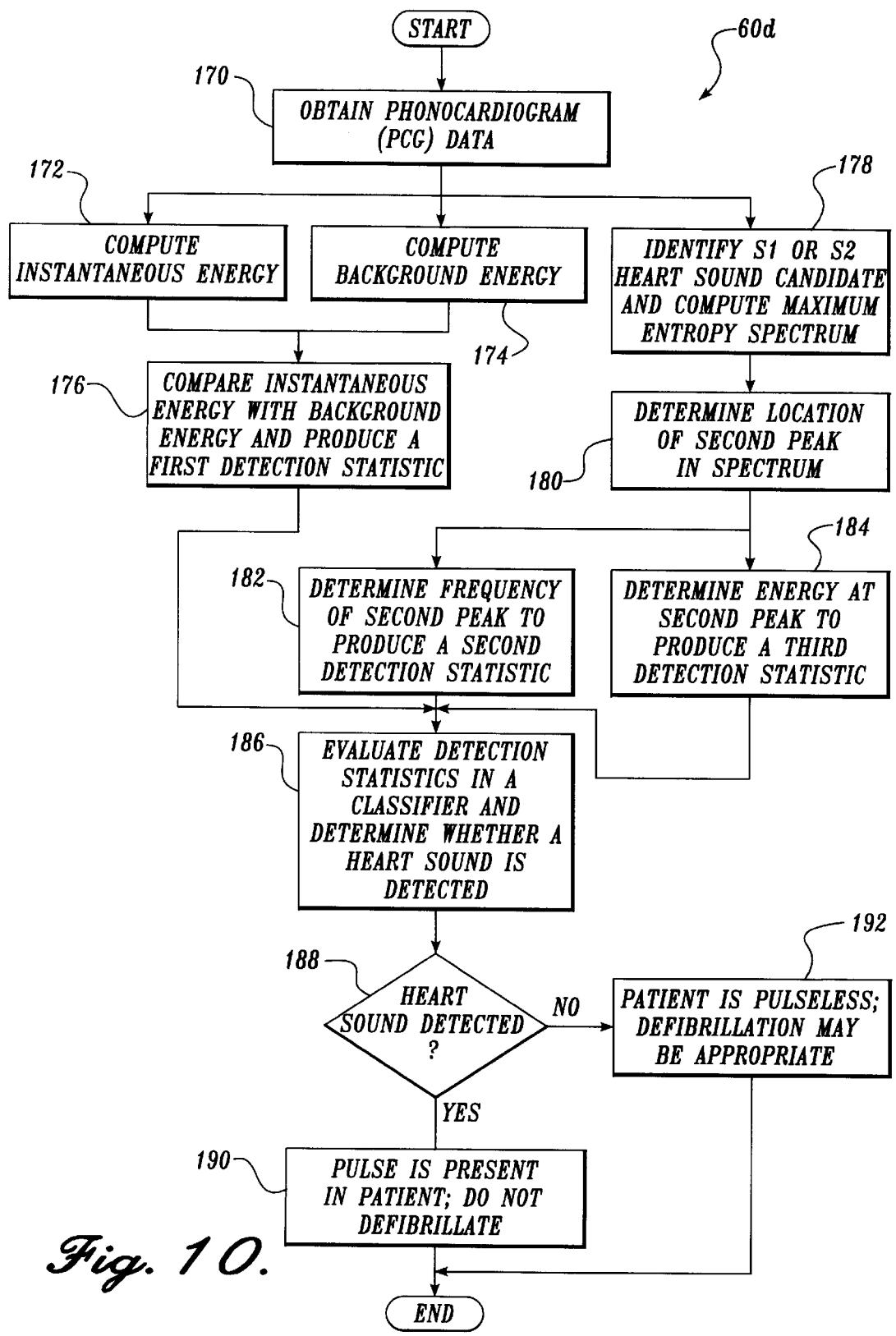
FIG. 10 is a flow diagram illustrating another pulse detection process performed by a defibrillator as shown in FIG. 2 that incorporates features of the pulse detection processes shown in FIGS. 4, 6 and 9.

On occasion, it is possible that noise in the PCG data may cause a false detection of a heart sound when using one of the versions 60a, 60b, or 60c of the pulse detection process described above. See, e.g., the two circled x's in FIGS. 8B and 8C immediately following the time reference of 0.6 seconds, which do not appear to correspond with heart sounds evident in FIG. 8A. If the signal-to-noise ratio of the PCG data obtained from the patient is not high enough to avoid such false detection of a heart sound using versions 60a, 60b, or 60c of the pulse detection process, the versions 60a, 60b, and 60c of the pulse detection process may be combined in one or more ways to produce a version of the pulse detection process that improves the specificity of the heart sound detection. FIG. 10 illustrates a version 60d of the pulse detection process that combines features of the versions 60a, 60b, and 60c of the pulse detection process.

In FIG. 10, the pulse detection process 60d begins in a block 170 by obtaining PCG data from a patient, e.g., in a manner as described earlier with respect to block 70 of pulse detection process 60a (FIG. 4). After the PCG data is obtained, estimates of the instantaneous energy and the background energy in the PCG data are computed in blocks 172 and 174, e.g., in a manner as described earlier with respect to blocks 72 and 74. The estimated instantaneous and background energy values are then compared in a block 176, e.g., as described earlier with respect to block 76, to produce a first detection statistic, or feature, indicative of the presence of a heart sound. The first detection statistic produced in block 176 is provided to a classifier in block 186 that evaluates detection statistics to determine whether a heart sound was present. Of course, those having ordinary skill in the art will recognize that the instantaneous and background energies computed in blocks 172 and 174 may also be directly provided as separate detection statistics to a multidimensional classifier in block 186 for joint classification with any other detection statistics provided to a multidimensional classifier (i.e., eliminating the comparison performed in block 176).

The PCG data obtained in block 170 is also used in identifying a heart sound candidate and computing an MEM spectrum in block 178, in a manner as described earlier with respect to blocks 102 and 104 of pulse detection process 60b (FIG. 6). Once the MEM spectrum is computed, the pulse detection process 60d determines in a block 180 the location of the second peak in the MEM spectrum.

The frequency of the second peak is determined in a block 182 and provided as a second detection statistic, or feature, to the classifier in block 186. Alternatively, the second detection statistic may be produced by comparing the frequency of the second peak with a threshold frequency, e.g., in a manner as described earlier with respect to block 108 (FIG. 6).

In a block 184, the pulse detection process 60d also determines the energy value at the second peak and provides the energy value as a third detection statistic, or feature, to the classifier in block 186. The second peak energy may alternatively be compared with a threshold energy, e.g., in a manner as described earlier with respect to block 160 (FIG. 9), to produce the third detection statistic.

The classifier in block 186 jointly classifies the first, second, and third detection statistics using a multidimensional classifier to determine whether a heart sound, and hence a pulse, is present in the patient. Techniques for constructing multidimensional classifiers are well-known in the art. For an expanded description of a classifier suitable for use in the present invention, see, e.g., R. Duda and P. Hart, *Pattern Classification and Scene Analysis*, published by John Wiley & Sons, New York, and incorporated herein by reference.

The classifier in block 186 may also use a voting scheme to determine whether a pulse is present in the patient. For example, if any of the first, second, or third detection statistics indicates the detection of a heart sound (i.e., the instantaneous energy exceeded the background energy by a threshold value, the frequency of the second peak was equal to or less than a threshold frequency, or the energy of the second peak exceeded a threshold energy), the classifier determines that a pulse is present in the patient. Alternatively, the classifier in block 186 may determine that a pulse is present by finding that a combination of the first, second, and third detection statistics indicates the presence of a heart sound (e.g., a positive indication from the first detection statistic combined with a positive indication from the second or third detection statistics, etc.). The classifier in block 186 may also weight the first, second, or third detection statistics to emphasize one detection statistic over another in deciding whether a heart sound was detected.

If, in a decision block 188, a heart sound was detected, the pulse detection process 60d determines in a block 190 that a pulse is present in the patient and advises the operator of the defibrillator to not defibrillate the patient. Otherwise, if a heart sound was not detected in decision block 188, the pulse detection process 60d determines in a block 192 that the patient is pulseless and that defibrillation therapy may be appropriate. An analysis of ECG data, as described earlier in reference to U.S. Pat. No. 4,610,254, may be used to determine if defibrillation therapy is appropriate.

Figure 11:
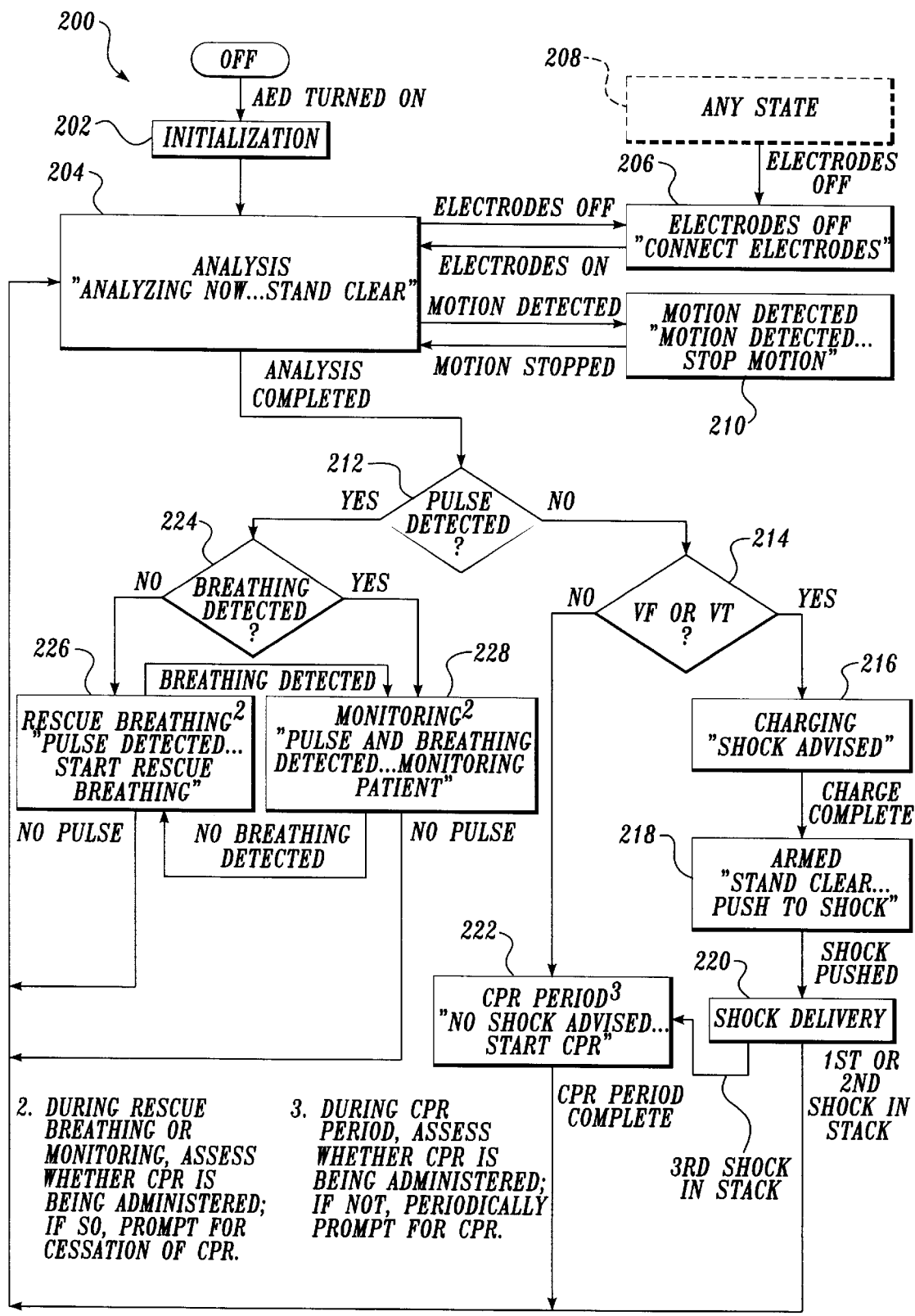
FIG. 11 is a flow diagram of a protocol implemented by a defibrillator as shown in FIG. 2 that incorporates a pulse detection process provided by the present invention.

As noted, the pulse detection process of the invention may be used as part of a protocol in a defibrillator for determining whether to provide defibrillation therapy to the patient. FIG. 11 illustrates one implementation of a pulse detection/defibrillation process 200, preferably for use in an automated external defibrillator (AED) capable of providing a defibrillation pulse if a patient is determined to be in cardiac arrest.

When an AED implementing the pulse detection/defibrillation process 200 is turned on, the process 200 proceeds to a block 202 where the AED initializes its circuits. The AED's PCG/defibrillation electrodes are placed on the patient. When the AED is ready for operation, the process 200 proceeds to a block 204 where the AED performs an analysis of the patient in which the AED obtains selected parameters such as PCG data and ECG data from the patient. During the analysis performed in block 204, the AED reports "Analyzing now . . . stand clear" to the operator of the AED.

If at any point the AED determines that the PCG/defibrillation electrodes are not connected to the AED, the process 200 jumps to a block 206 where the AED instructs the operator to "Connect electrodes." When the AED senses that the electrodes are connected, the process 200 returns to the analysis in block 204. Likewise, if the AED finds itself in any other state where the electrodes are not connected, as represented by block 208, the process 200 jumps to block 206 where it instructs the operator to connect the electrodes.

Furthermore, during the analysis performed in block 204, if the AED detects motion on the part of the patient, the process 200 proceeds to a block 210 where the AED reports to the operator of the AED "Motion detected . . . stop motion." If the patient is moved during the analysis process 204, the data obtained during the analysis is more likely to be contaminated with noise and other signal contaminants. In one actual embodiment of the invention, motion on the part of the patient is detected by an impedance channel that evaluates the impedance measured between the PCG/defibrillation electrodes placed on the patient. If the measured impedance fluctuates outside of a predetermined range, the AED determines that the patient is moving and directs the process 200 to proceed to block 210. When the motion ceases, the process 200 returns to the analysis in block 204.

Once the analysis in block 204 is completed, the process 200 proceeds to a decision block 212 where it determines whether a pulse is detected in the patient. The pulse detection performed in block 212 may be any one or combination of the versions 60a, 60b, 60c, or 60d of the pulse detection process described above, and may involve an analysis of a physiological signal sensed in the patient other than acoustical energy (PCG data).

If a pulse is not detected in the patient, the process 200 proceeds to a decision block 214 where it determines whether the patient has a shockable cardiac rhythm (e.g., ventricular fibrillation (VF) or ventricular tachycardia (VT)) or a non-shockable cardiac rhythm (such as asystole and bradycardia). As referenced earlier, one suitable method for differentiating shockable from non-shockable cardiac rhythms is disclosed in U.S. Pat. No. 4,610,254.

If the patient's cardiac rhythm is determined to be shockable, the process 200 proceeds to a block 216 where the AED prepares to deliver a defibrillation pulse to the patient. In that regard, an energy storage device such as a capacitor bank, within the AED is charged to a specified level. At the same time, the AED reports "Shock advised" to the operator of the AED.

Once the energy storage device is fully charged, the process 200 proceeds to a block 218 where the AED is ready to deliver the defibrillation pulse. The operator of the AED is advised "Stand clear . . . push to shock." When the operator of the AED initiates delivery of the defibrillation pulse, the process 200 proceeds to block 220 and delivers the defibrillation shock to the patient. After delivery of the defibrillation pulse, the AED preferably records in memory that it delivered a defibrillation pulse to the patient. If the present pulse delivery is the first or second defibrillation shock delivered to the patient, the process 200 returns to block 204 where the patient undergoes another analysis. On the other hand, if the pulse delivery was the third defibrillation pulse to be delivered to the patient, the process 200 proceeds to a block 222 where the AED advises the operator to commence providing CPR therapy to the patient, e.g., by using the message "No shock advised . . . start CPR."

Returning to decision block 214, if a non-shockable cardiac rhythm is found in the patient, the process 200 proceeds to block 222 and advises the operator to provide CPR therapy. Again, at this point, the AED reports "No shock advised . . . start CPR" to the operator. Preferably, the prompt to provide CPR is provided for a defined period of time. When the period of time for CPR is finished, the process 200 returns to block 204 and performs another analysis on the patient.

Returning to decision block 212, if a pulse is detected in the patient, the process 200 proceeds to a decision block 224 where it determines whether the patient is breathing. In that regard, the AED may use any one of a number of conventional means for automatically determining whether a patient is breathing. Such means include attaching a sample tube by the patient's mouth to analyze fluctuations in carbon dioxide exhaled by the patient. Other means include observing changes in impedance of the patient that are indicative of a change in volume in the patient's lungs. Other means also include stretching a band with a strain gauge around the patient's chest to observe expansion of the patient's chest due to breathing. Alternatively, if automatic means for detecting breathing in the patient are not available, the AED may ask the operator of the AED to input information (e.g., by pressing a button) to indicate whether the patient is breathing.

If, in decision block 224, the process 200 determines that the patient is not breathing, the process 200 proceeds to a block 226 where the operator of the AED is advised to commence rescue breathing. In that regard, the AED reports to the operator "Pulse detected . . . start rescue breathing." The AED also continues to monitor the patient's cardiac pulse and returns to block 204 if a cardiac pulse is no longer detected. If, at any point during the provision of rescue breathing, the AED detects that the patient is breathing on his own, the process 200 proceeds to a block 228 where the AED monitors the patient for a continued presence of breathing and a cardiac pulse.

Returning to decision block 224, if the process 200 determines that the patient is breathing, the process 200 proceeds to block 228 where the AED monitors the status of the patient. In that regard, the AED reports "Pulse and breathing detected . . . monitoring patient." If, at any time during the monitoring of the patient the process 200 determines that the patient is not breathing, the process 200 proceeds to block 226 where the operator of the AED is advised to commence rescue breathing. If a cardiac pulse is no longer detected in the patient, the process 200 proceeds from block 228 to block 204 to commence a new analysis of the patient.

Lastly, as noted in FIG. 11, during the rescue breathing procedure in block 226 or the monitoring procedure performed in block 228, the AED may assess whether CPR is being administered to the patient. If the AED finds that CPR is being performed, the AED may prompt the operator to cease providing CPR. If, during the CPR period of block 222, the AED determines that CPR is not being administered to the patient, the AED may remind the operator to provide CPR therapy to the patient. One method for determining whether CPR is being administered is to monitor patient impedance to observe patterns of impedance fluctuation in the patient that are indicative of CPR.

As discussed earlier, an analysis of ECG data may be combined with an analysis of PCG data to determine the presence of a cardiac pulse in the patient. In one aspect, detecting a QRS complex in the ECG data preceding the time that a heart sound occurs may serve to confirm the detection of the heart sound. In another aspect, detecting a QRS complex in the ECG data may be used to identify PCG data for use in the heart sound detection process, since a heart sound is expected to occur after the occurrence of a QRS complex if a cardiac pulse is present in the patient. This aspect of the invention is helpful in identifying a heart sound candidate in the PCG data. It is also helpful in identifying whether the patient is in a state of pulseless electrical activity. If a QRS complex is found in the ECG data and a heart sound does not occur within an expected time period thereafter, the patient is in a state of pulseless electrical activity that may be reported to the operator of the device (e.g., along with the CPR advisory in block 222 of the pulse detection/defibrillation process 200 shown in FIG. 11).

While various embodiments of the invention have been illustrated and described, it will be appreciated that various changes can be made to those embodiments without departing from the spirit and scope of the invention. For example, while the pulse detection processes described in detail herein primarily use an analysis of PCG data to determine the presence of a cardiac pulse, it is recognized that the pulse detection processes may analyze data obtained from other physiological signals sensed in the patient for features indicative of the presence of a cardiac pulse. For instance, variations in the patient's transthoracic impedance may be associated with the discharge of blood from the heart. By monitoring characteristic variations in the patient's transthoracic impedance, the pulse detection process may monitor the patient's cardiac output, and hence determine the presence of a cardiac pulse. Ultrasound signals from Doppler ultrasound probes placed on the patient may also be used to monitor and quantify blood flow in the patient, and hence determine the presence of a cardiac pulse.

Furthermore, while using an MEM spectrum for a spectral analysis of PCG data is described in detail herein, those of ordinary skill in the art will appreciate that other spectral analysis techniques, including those based on a Fourier transform, may be used instead. Moreover, as noted, the temporal energy aspect and the spectral energy aspect of the invention may be separately or jointly applied to determine whether a heart sound is present in the patient. It is intended, therefore, that the scope of the invention be determined by the following claims and equivalents thereto.

The embodiments of the invention in which an exclusive property or privilege is claimed are defined as follows:

1. A method of determining the presence of a cardiac pulse in a patient, comprising:
   (a) obtaining phonocardiogram (PCG) data from the patient;
   (b) analyzing the PCG data for a feature indicative of the presence of a heart sound;
   (c) determining whether a heart sound is present in the patient based on the feature; and
   (d) determining whether a cardiac pulse is present in the patient based on the determination of whether a heart sound is present in the patient.

2. The method of claim 1, wherein analyzing the PCG data includes evaluating temporal energy in the PCG data.

3. The method of claim 2, wherein evaluating temporal energy in the PCG data includes:
   (a) estimating an instantaneous energy in the PCG data;
   (b) estimating a background energy in the PCG data; and
   (c) comparing the estimated instantaneous energy with the estimated background energy to produce the feature indicative of the presence of a heart sound.

4. The method of claim 1, wherein analyzing the PCG data includes evaluating spectral energy in the PCG data.

5. The method of claim 4, wherein evaluating spectral energy in the PCG data includes calculating an energy spectrum of the PCG data and evaluating the energy spectrum to locate a peak energy value, wherein the located peak energy value is used as the feature indicative of the presence of a heart sound, and wherein determining whether a heart sound is present in the patient includes comparing the located peak energy value with a threshold energy value.

6. The method of claim 5, wherein the energy spectrum includes multiple peak energy values and the located peak energy value is the second peak energy value measured from a baseline frequency.

7. The method of claim 4, wherein evaluating spectral energy in the PCG data includes calculating an energy spectrum of the PCG data, evaluating the energy spectrum to locate a peak energy value, and determining the frequency at which the peak energy value occurs, wherein the frequency of the peak energy value is used as the feature indicative of the presence of a heart sound, and wherein determining whether a heart sound is present in the patient includes comparing the frequency of the peak energy value with a threshold frequency.

8. The method of claim 7, wherein the energy spectrum includes multiple peak energy values and the located peak energy value is the second peak energy value measured from a baseline frequency.

9. The method of claim 1, further comprising:
   (a) repeating the steps of obtaining PCG data, analyzing the PCG data for a feature indicative of the presence of a heart sound, and determining whether a heart sound is present based on the feature, to produce two or more determinations of the presence of a heart sound; and
   (b) determining the presence of a cardiac pulse in the patient based on the number of determinations indicating the presence of a heart sound.

10. A method of determining the presence of a heart sound in a patient, comprising:
    (a) obtaining phonocardiogram (PCG) data from the patient;
    (b) estimating a first energy in the PCG data;
    (c) estimating a second energy in the PCG data;
    (d) determining a relative change in energy between the first energy and the second energy; and
    (e) determining the presence of a heart sound in the patient based on the determined relative change in energy.

11. The method of claim 10, wherein the first energy is estimated using a first set of PCG data and the second energy is estimated using a second set of PCG data, and wherein the second set of PCG data is obtained prior to the first set of PCG data.

12. The method of claim 10, further comprising:
    (a) calculating an energy spectrum of the PCG data;
    (b) evaluating the energy spectrum for a spectral energy feature indicative of the presence of a heart sound; and
    (c) determining the presence of a heart sound in the patient based on the determined relative change in energy and the spectral energy feature.

13. The method of claim 10, further comprising:
    (a) obtaining electrocardiogram (ECG) data from the patient;
    (b) determining the presence of a QRS complex in the ECG data; and
    (c) determining the presence of a heart sound in the patient based on a relationship between the presence of a QRS complex in the ECG data and the presence of a heart sound in the PCG data.

14. The method of claim 13, wherein the presence of a QRS complex in the ECG data is used in identifying the PCG data to be used in determining the presence of a heart sound.

15. The method of claim 13, further comprising determining whether the patient is in a state of pulseless electrical activity based on the presence of a QRS complex in the ECG data and a lack of presence of a heart sound in the PCG data.

16. The method of claim 15, further comprising producing a report indicating whether the patient is in a state of pulseless electrical activity.

17. The method of claim 10, further comprising producing a report recommending against provision of defibrillation therapy if a heart sound is determined to be present in the patient.

18. A method of determining the presence of a heart sound in a patient, comprising:
    (a) obtaining phonocardiogram (PCG) data from the patient;
    (b) calculating an energy spectrum of the PCG data;
    (c) evaluating the energy spectrum for a spectral energy feature indicative of the presence of a heart sound; and
    (d) determining the presence of a heart sound in the patient based on the spectral energy feature.

19. The method of claim 18, wherein the spectral energy feature is a peak energy value in the energy spectrum.

20. The method of claim 19, wherein determining the presence of a heart sound includes comparing the peak energy value with a threshold energy value.

21. The method of claim 20, wherein the peak energy value is the second peak energy value occurring in the energy spectrum measured from a baseline frequency.

22. The method of claim 19, wherein determining the presence of a heart sound includes evaluating the frequency at which the peak energy value occurs in the energy spectrum.

23. The method of claim 22, wherein evaluating the frequency at which the peak energy value occurs includes comparing the frequency of the peak energy value with a threshold frequency.

24. The method of claim 22, wherein the peak energy value is the second peak energy value occurring in the energy spectrum measured from a baseline frequency.

25. The method of claim 18, further comprising identifying a set of PCG data that has a higher likelihood of containing a heart sound, and using the set of PCG data to calculate the energy spectrum.

26. The method of claim 18, further comprising:
   (a) obtaining electrocardiogram (ECG) data from the patient;
   (b) determining the presence of a QRS complex in the ECG data; and
   (c) determining the presence of a heart sound in the patient based on a relationship between the presence of a QRS complex in the ECG data and the presence of a heart sound in the PCG data.

27. The method of claim 26, wherein the presence of a QRS complex in the ECG data is used in identifying the PCG data to be used in determining the presence of a heart sound.

28. The method of claim 26, further comprising determining whether the patient is in a state of pulseless electrical activity based on the presence of a QRS complex in the ECG data and a lack of presence of a heart sound in the PCG data.

29. The method of claim 28, further comprising producing a report indicating whether the patient is in a state of pulseless electrical activity.

30. The method of claim 18, wherein the energy spectrum is calculated using a maximum entropy method.

31. The method of claim 18, further comprising determining the presence of a cardiac pulse in the patient based on the determined presence of a heart sound in the patient.

32. The method of claim 18, wherein the spectral energy feature is a first spectral energy feature, the method further comprising evaluating the energy spectrum for a second spectral energy feature indicative of the presence of a heart sound, wherein determining the presence of a heart sound in the patient is based on the first and second spectral energy features.

33. The method of claim 32, wherein the first spectral energy feature is a peak energy value in the energy spectrum, and wherein the second spectral energy feature is the frequency at which a peak energy value occurs in the energy spectrum.

34. The method of claim 33, wherein the first spectral energy feature is the peak energy value of the second peak energy in the energy spectrum measured from a baseline frequency, and the second spectral energy feature is the frequency at which the second peak energy occurs in the energy spectrum.

35. The method of claim 34, wherein determining the presence of a heart sound in the patient includes comparing the peak energy value of the second peak energy with a threshold energy value, and comparing the frequency of the second peak energy with a threshold frequency.

36. The method of claim 18, further comprising producing a report recommending against provision of defibrillation therapy if a heart sound is determined to be present in the patient.

37. The method of claim 18, further comprising evaluating temporal energy in the PCG data for a temporal energy feature, wherein determining the presence of a heart sound in the patient is based on the spectral energy feature and the temporal energy feature.

38. The method of claim 37, wherein the temporal energy feature is determined by:

(a) estimating a first energy in the PCG data;
(b) estimating a second energy in the PCG data; and
(c) determining a relative change in energy between the first energy and the second energy.

39. The method of claim 38, wherein the first energy is estimated using a first set of PCG data and the second energy is estimated using a second set of PCG data, and wherein the second set of PCG data is obtained prior to the first set of PCG data.

40. The method of claim 37, wherein the temporal energy feature is based on an estimated energy in the PCG data, and wherein the spectral energy feature is based on a peak energy value in the energy spectrum.

41. The method of claim 37, wherein the temporal energy feature and the spectral energy feature are jointly classified in a multi-dimensional classifier to determine whether a heart sound is present in the patient.

42. The method of claim 41, wherein the temporal energy feature or the spectral energy feature is weighted to emphasize one feature over the other.

43. A medical device, comprising:
   (a) a phonocardiogram (PCG) electrode adapted to sense PCG signals in a patient;
   (b) a conversion circuit in communication with the PCG electrode for converting the PCG signals into digital PCG data; and
   (c) a processing unit in communication with the conversion circuit for processing the digital PCG data, the processing unit operating in accordance with programmed instructions to analyze the PCG data and determine a feature indicative of the presence of a heart sound in the patient, the processing unit evaluating the determined feature to determine the presence of a heart sound and further determine the presence of a cardiac pulse in the patient based on the determined presence of a heart sound.

44. The medical device of claim 43, further comprising a display in communication with the processing unit, wherein the processing unit is configured to prompt a message on the display reporting whether a cardiac pulse is determined to be present in the patient.

45. The medical device of claim 43, further comprising a defibrillation pulse generator in communication with the processing unit for delivering a defibrillation pulse to the patient if the processing unit determines that a cardiac pulse is not present in the patient.

46. The medical device of claim 45, wherein the medical device is an automated external defibrillator and the processing unit is configured to automatically obtain and analyze PCG data from the patient to determine the presence of a cardiac pulse in the patient.

47. The medical device of claim 45, further comprising an input device that allows an operator of the medical device to initiate delivery of the defibrillation pulse if the processing unit determines that a cardiac pulse is not present in the patient.

48. The medical device of claim 43, wherein the feature indicative of the presence of a heart sound is a temporal energy feature.

49. The medical device of claim 48, wherein the temporal energy feature is determined by the processing unit from a determination of a relative change in energy between an estimated first energy in the PCG data and an estimated second energy in the PCG data.

50. The medical device of claim 49, wherein the first energy is estimated using a first set of PCG data and the second energy is estimated using a second set of PCG data, and wherein the second set of PCG data is obtained prior to the first set of PCG data.

51. The medical device of claim 43, wherein the feature indicative of the presence of a heart sound is a spectral energy feature.

52. The medical device of claim 51, wherein the spectral energy feature is determined by the processing unit from a calculation of an energy spectrum of the PCG data and the location of a peak energy in the energy spectrum, wherein the energy value of the located peak energy is used as the spectral energy feature.

53. The medical device of claim 51, wherein the spectral energy feature is determined by the processing unit from a calculation of an energy spectrum of the PCG data and the location of a peak energy in the energy spectrum, wherein the frequency at which the located peak energy occurs is used as the spectral energy feature.

54. The medical device of claim 43, wherein the feature indicative of the presence of a heart sound is a first feature, and wherein the processing unit further operates in accordance with programmed instructions to analyze the PCG data and determine a second feature indicative of the presence of a heart sound, the processing unit determining the presence of a heart sound by evaluating the first and second features.

55. The medical device of claim 54, wherein the first feature and the second feature are a temporal energy feature or a spectral energy feature derived from the PCG data.

56. The medical device of claim 43, further comprising a plurality of electrocardiogram (ECG) electrodes adapted to sense ECG signals in the patient, wherein the ECG electrodes are in communication with a conversion circuit for converting the ECG signals into digital ECG data that is provided to the processing unit, the processing unit operating in accordance with programmed instructions to analyze the ECG data and determine the presence of a QRS complex in the ECG data, the processing unit determining the presence of a cardiac pulse in the patient if a QRS complex occurs in the ECG data within an expected time period preceding the occurrence of a heart sound in the PCG data.

57. The medical device of claim 56, wherein the occurrence of a QRS complex in the ECG data is used in identifying the PCG data to be used in determining the presence of a heart sound.

58. The medical device of claim 56, further comprising a defibrillation pulse generator in communication with the processing unit, wherein the processing unit is configured to instruct the defibrillation pulse generator to generate a defibrillation pulse if the processing unit determines that a cardiac pulse is not present in the patient and that the ECG data obtained from the patient indicates a cardiac rhythm appropriate for treatment by defibrillation therapy.

59. The medical device of claim 56, further comprising a display in communication with the processing unit, wherein the processing unit is configured to prompt a message on the display recommending application of cardiopulmonary resuscitation (CPR) to the patient if the processing unit determines that a cardiac pulse is not present in the patient and that the ECG data obtained from the patient does not indicate a cardiac rhythm appropriate for treatment by defibrillation therapy.

60. The medical device of claim 59, wherein the processing unit is configured to track the delivery of defibrillation pulses to the patient and prompt a message on the display recommending application of CPR to the patient if the number of defibrillation pulses delivered to the patient equals or exceeds a predetermined number.

61. The medical device of claim 59, wherein the processing unit is configured to prompt a message on the display reporting that the patient is in a state of pulseless electrical activity if a QRS complex occurs in the ECG data and a heart sound does not occur in the PCG data.

62. The medical device of claim 59, wherein if the processing unit determines that a cardiac pulse is present in the patient, the processing unit prompts a message on the display recommending application of rescue breathing therapy to the patient if the patient is also not breathing.

* * * * *